US009427171B2

United States Patent
Gdaniec et al.

(10) Patent No.: US 9,427,171 B2
(45) Date of Patent: Aug. 30, 2016

(54) MAGNETIC RESONANCE IMAGE RECONSTRUCTION METHOD WITH RESPIRATORY MOT DETECTION DURING SAMPLING OF CENTRAL AND PERIPHERAL K-SPACE AREAS

(71) Applicant: KONINKLIJKE PHILIPS N.V., Eindhoven (NL)

(72) Inventors: Nadine Gdaniec, Eindhoven (NL); Holger Eggers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 15 days.

(21) Appl. No.: 14/385,182

(22) PCT Filed: Feb. 22, 2013

(86) PCT No.: PCT/IB2013/051449
§ 371 (c)(1),
(2) Date: Sep. 15, 2014

(87) PCT Pub. No.: WO2013/140276
PCT Pub. Date: Sep. 26, 2013

(65) Prior Publication Data
US 2015/0073263 A1 Mar. 12, 2015

Related U.S. Application Data

(60) Provisional application No. 61/612,522, filed on Mar. 19, 2012.

(51) Int. Cl.
*A61B 5/055* (2006.01)
*G01R 33/48* (2006.01)
(Continued)

(52) U.S. Cl.
CPC ............... *A61B 5/055* (2013.01); *A61B 5/08* (2013.01); *A61B 5/7285* (2013.01); *G01R 33/385* (2013.01); *G01R 33/4818* (2013.01); *G01R 33/546* (2013.01); *G01R 33/567* (2013.01);
(Continued)

(58) Field of Classification Search
CPC ...... A61B 5/055; A61B 5/08; A61B 5/7285; G01R 33/385; G01R 33/4818; G01R 33/4824; G01R 33/546; G01R 33/5611; G01R 33/56509; G01R 33/567; G01R 33/5673
See application file for complete search history.

(56) References Cited

U.S. PATENT DOCUMENTS 6,292,684 B1 * 9/2001 Du .................... G01R 33/5676
324/309
6,611,701 B2 8/2003 Foo
(Continued)

OTHER PUBLICATIONS

Weller, Daniel S. et al "Combined Compressed Sensing and Parallel MRI Compared for Uniform and Random Cartesian Undersampling of K-Space", Acoustics, Speech and Signal Processing, 2011 IEEE Int'l Conf.

(Continued)

*Primary Examiner* — Ruth S Smith (57) ABSTRACT

A magnetic resonance image of a subject is generated by acquiring k-space samples by sampling an elliptical central area of k-space, k-space having a plurality of points. Each point is representative of a potential sample. An elliptical peripheral area of k-space which peripheral area surrounds the central area is partially sampled. Respiratory motion of the subject is detected and the magnetic resonance image of the subject is reconstructed using the k-space samples acquired before the detection of respiratory motion.

7 Claims, 7 Drawing Sheets

(51) Int. Cl.
| | |
|---|---|
| G01R 33/565 | (2006.01) |
| G01R 33/567 | (2006.01) |
| A61B 5/08 | (2006.01) |
| A61B 5/00 | (2006.01) |
| G01R 33/385 | (2006.01) |
| G01R 33/54 | (2006.01) |
| G01R 33/561 | (2006.01) |

(52) U.S. Cl.
CPC ..... *G01R 33/5673* (2013.01); *G01R 33/56509* (2013.01); *G01R 33/4824* (2013.01); *G01R 33/5611* (2013.01)

(56) References Cited

U.S. PATENT DOCUMENTS

| | | | |
|---|---|---|---|
| 7,199,582 | B2 | 4/2007 | Keegan |
| 2009/0274356 | A1 | 11/2009 | Ying |

OTHER PUBLICATIONS

Moghari, Mehdi H. et al "Compressed-Sensing Motion Compensation (CosMo): A Joint Prospecitive-Retrospective Respiratory Navigator for Coronary MRI", Magnetic Resonance in Medicine. vol. 66, No. 6, Jun. 2011, pp. 1675-1678.

Gdaniec, Nadine et al "Novel Sampling Strategy for Abdominal Imaging with Incomplete Breathholds", Proc. Intl. Society Magnetic Resonance in Medicine, vol. 20, 2012, pp. 600.

Lai, P. et al "Improving Compressed Sensing Parallel Imaging using Autocalibrating Parallel Imaging Initialization with Variable Density Tiled Random K-Space Sampling" Proc. Intl. Society Magnetic Resonance in Medicine, vol. 19, Apr. 2011 pp. 68.

Bullmore, E. et al "Wavelets and Functional Magnetic Resonance Imaging of the Human Brain" Neuroimage, vol. 23, Jan. 2004, pp. S234-S249.

Sachs, T.S. et al "Real-Time Motion Detection in Spiral MRI using Navigators" Magnetic Resonance in Medicine, vol. 33, Jan. 1994, pp. 639-645.

Wang, Y. et al "Navigator-Echo-Based Real-Time Respiratory Gating and Triggering for Reduction of Respiration Effects in Three-Dimensional Coronary MR Angiography", Radiology, Radiological Society of North America, vol. 198, No. 1, Jan. 1996, pp. 55-60.

Wang, Zhongmin et al "Variable Density Compressed Image Sampling", IEEE. Transaction on Image Processing, vol. 19, No. 1, Jan. 2010. pp. 264-270.

Dunbar, Daniel et al "A Spatial Data Structure for Fast Poisson-Disk Sample Generation", Proc. SIGGRAPH, 2006, pp. 503-508.

Maki, Jeffrey H. et al "The Effects of Incomplete Breath-Holding on 3D MR Image Quality", Journal Magnetic Resonance in Imaging, vol. 7, 1997, pp. 1132-1139.

Lustig, Michael et al "Sparse MRI: The Application of Compressed Sensing for Rapid MR Imaging", Magnetic Resonance in Medicine, vol. 58, 2007, pp. 1182-1195.

\* cited by examiner

MAGNETIC RESONANCE IMAGE RECONSTRUCTION METHOD WITH RESPIRATORY MOT DETECTION DURING SAMPLING OF CENTRAL AND PERIPHERAL K-SPACE AREAS

CROSS-REFERENCE TO PRIOR APPLICATIONS

This application is the U.S. National Phase application under 35 U.S.C. §371 of International Application No. PCT/IB2013/051449, filed on Feb. 22, 2013, which claims the benefit of U.S. Provisional Patent Application No. 61/612,522, filed on Mar. 19, 2012. These applications are hereby incorporated by reference herein.

TECHNICAL FIELD

The invention relates to the field of magnetic resonance imaging of a subject.

BACKGROUND OF THE INVENTION

Magnetic resonance imaging (MRI) methods use the interaction between magnetic field and nuclear spins with the purpose of forming two-dimensional or three-dimensional images. These methods are widely used these days, notably in the field of medical diagnostics. The advantages of the MR methods are that they do not require ionizing radiation and they are usually not invasive. MRI is used for example as imaging technique to visualize structural abnormalities of the body, e.g. tumour development.

An MRI apparatus uses a powerful magnetic field to align the magnetization of some atomic nuclei in the body, and radio frequency fields to systematically modify the alignment of this magnetization. This causes the nuclei to produce a rotating magnetic field detectable by a scanner. This information is recorded to construct an image of the sampled area of the body. Magnetic field gradients cause nuclei at different locations to rotate at different speeds. By using gradients in different directions 2D images or 3D volumes can be obtained in arbitrary orientation.

According to the MR method in general, the body of a patient or in general an object to be examined is arranged in a strong, uniform magnetic field B0 whose direction at the same time defines an axis, normally the z-axis, of the coordinate system on which the measurement is based.

Any temporal variation of the magnetization can be detected by means of receiving RF antennas, which are configured and oriented within an examination volume of the MR device in such a manner that the temporal variation of the magnetization is measured in the direction vertically to the z-axis.

Spatial resolution in the body can be realized by switching magnetic field gradients. They extend along the three main axes and are superposed on the uniform magnetic field, leading to a linear spatial dependency of the spin resonance frequency. The signal picked up in the receiving antennas then comprises components of different frequencies which can be linked to different locations in the body/subject.

The signal data obtained by the receiving antennas matches to the spatial frequency domain and are called k-space data. The k-space data generally include multiple lines acquired with different phase encoding. Each line is digitized by collecting a number of samples. A set of samples of k-space data is transformed to an MR image, e.g. by inverse Fourier transformation.

Furthermore the document "Combined compressed sensing and parallel MRI compared for uniform and random cartesian undersampling of k-space" by D. S. Weller et al. (2011 IEEE Int. Conf. on Acoustics, Speech, and Signal Processing. Prague, Czech Republic, May 2011, pp. 553-6) discloses the combination of compressed sensing and variable density random k-space sampling. Combining both methods enables imaging with greater undersampling than accomplished previously.

United States Published Application US 20090274356 A1 describes a method for generating a magnetic resonance image of a subject. The disclosed invention relates to magnetic resonance imaging using compressed sensing which allows recovery of a sparse signal, or a signal that can be made sparse by transformations, from a highly incomplete set of samples, and thus has the potential for significant reduction in MRI scan time.

SUMMARY OF THE INVENTION

The invention provides for a method, a medical apparatus, and a computer program product that are claimed in the independent claims. Embodiments are given in the dependent claims.

In accordance with embodiments of the invention a sampling strategy for magnetic resonance imaging with incomplete breathholds is provided which supports the reconstruction of images from data acquired up to any point in time. It proposes to combine a segmented acquisition with global sampling density variation and local Poisson disk sampling. The sampling strategy is thus compatible with compressed sensing and parallel imaging for accelerated scanning, and adaptable to target functions of the spatial resolution over time. The onset of respiratory motion is either detected with external or internal sensors, or is based on metrics applied to a series of images, produced from successively more data.

In accordance with embodiments of the invention a method of generating a magnetic resonance image of a subject is provided comprising the acquisition of k-space samples by sampling an elliptical central area of k-space, wherein the k-space has a plurality of points, each point being representative of a potential sample and partially sampling an elliptical peripheral area of k-space, wherein the peripheral area surrounds the central area. The method further comprises the detection of respiratory motion of the subject and reconstruction of the magnetic resonance image of the subject using the k-space samples acquired before the detection of respiratory motion.

Embodiments of the invention are particularly advantageous as they provide a reconstruction of images from data acquired during breathholds with a priori unknown length. This reconstruction avoids artifacts and thus a decrease in image quality resulting from previously methods in the case of early onset of respiratory motion. It relies on a specific profile order which makes it possible to exclude data acquired after the onset of respiratory motion from the reconstruction.

In accordance with one embodiment of the invention the central area is fully sampled.

In general, artifacts resulting from incomplete breathholds are less severe if respiratory motion occurs during sampling of the periphery of k-space, rather than the center of k-space. Thus, embodiments of the invention are particularly advantageous as they sample the central k-space fully and early on, thus reducing the risk of more severe motion artifacts.

In accordance with one embodiment of the invention the method further comprises increasing the half-axes of the peripheral area during the acquisition over time for increasing spatial resolution over time.

Embodiments of the invention are particularly advantageous as they provide a procedure that the sampling density increases over time, corresponding to a decreasing average reduction factor over time leading to a higher image quality.

In accordance with one embodiment of the invention the method further comprises that the partial sampling is performed by random or pseudo-random selection of a subset of the plurality of points being located in the peripheral area.

In accordance with one embodiment of the invention the likelihood of selecting one of the plurality of points that has not been previously selected is defined by a k-space and time variant target sampling density.

Embodiments of the invention are particularly advantageous as they provide a procedure that the sampling density becomes locally nearly homogeneous, facilitating a parallel imaging reconstruction leading to a higher quality of the reconstructed image. The term sampling density means herein the density of the sampled points.

In accordance with one embodiment of the invention the selection of one of the plurality of points that has not been previously selected is based on k-space and time variant minimum distances to all points that have already been selected.

Embodiments of the invention are particularly advantageous as they provide a procedure that the quality of the reconstructed image becomes better due to the above mentioned sampling density which is locally nearly homogenous.

In accordance with one embodiment of the invention the sequence of selected points is grouped into subsequences, wherein the selected points in each subsequence are permuted to minimize artifacts resulting from system and acquisition imperfections.

In accordance with one embodiment of the invention the points in each subsequence are permuted to minimize the distance in k-space between points acquired in immediate succession.

Embodiments of the invention are particularly advantageous as they provide a procedure that eddy current effects in the acquisition can be minimized leading to reduced artifacts arising from eddy currents.

In accordance with one embodiment of the invention the number of selected points in each subsequence is defined with a target maximum average reduction factor.

Embodiments of the invention are particularly advantageous as they provide a procedure that the reduction factor is successively reduced which also provides a better image reconstruction.

In accordance with one embodiment of the invention the sampling density decreases towards the periphery of k-space.

Embodiments of the invention are particularly advantageous as they provide a procedure that the fully sampled central area increases over time leading to the best available image.

In accordance with one embodiment of the invention the respiratory motion is detected using a magnetic resonance navigator, wherein moving of the diaphragm or the abdomen of the subject is detected, wherein the detection is performed simultaneously or interleaved with the imaging and wherein the acquisition is automatically stopped when respiratory motion of the subject is detected.

The duration an individual patient can actually hold his/her breath is unknown and generally unpredictable. Embodiments of the invention are particularly advantageous as they relieve the operator from guessing this duration prior to the examination and from repeating the examination in case of an overestimation.

In accordance with one embodiment of the invention the magnetic resonance images are reconstructed by using the k-space samples acquired before a certain point in time, wherein this point in time is successively increased, and the last image without significant artifacts is taken as the result, wherein a compressed sensing or parallel imaging reconstruction, or a combination of both, is employed for generating the magnetic resonance image.

Embodiments of the invention are particularly advantageous as they provide a procedure that it enables an efficient reconstruction of images from sparse, incomplete data using both compressed sensing and parallel imaging.

In accordance with one embodiment of the invention the k-space samples are acquired using a magnetic resonance gradient-echo, spin-echo, echo-planar imaging or diffusion-weighted imaging sequence.

Embodiments of the invention are particularly advantageous as they provide a procedure that enables the users to use the best technique for a specific application. The advantage of gradient-echo techniques is primarily a faster acquisition, while spin-echo sequences provide a stronger signal and are more robust against artifacts. Echo planar imaging is even faster than conventional gradient-echo techniques, at the expense of even more artifacts. Diffusion-weighted imaging provides unique contrast between tissues and insights into cellular architecture at the millimeter scale, which is of particular interest in the field of oncology.

The invention provides a medical apparatus for generating a magnetic resonance image of a subject comprising the acquisition of k-space samples by sampling an elliptical central area of k-space, wherein the k-space has a plurality of points, each point being representative of a potential sample and partially sampling an elliptical peripheral area of k-space, wherein the peripheral area surrounds the central area. The medical apparatus further comprises the ability for detection of respiratory motion of the subject and reconstruction of the magnetic resonance image of the subject using the k-space samples acquired before the detection of respiratory motion.

The invention provides a computer program product for generating a magnetic resonance image of a subject comprising the acquisition of k-space samples by sampling an elliptical central area of k-space, wherein the k-space has a plurality of points, each point being representative of a potential sample and partially sampling an elliptical peripheral area of k-space, wherein the peripheral area surrounds the central area. The computer program product further comprises the ability for detection of respiratory motion of the subject and reconstruction of the magnetic resonance image of the subject using the k-space samples acquired before the detection of respiratory motion.

BRIEF DESCRIPTION OF THE DRAWINGS

In the following embodiments of the invention will be described, by way of example only, and with reference to the drawings in which.

DETAILED DESCRIPTION OF THE EMBODIMENTS

Figure 1:
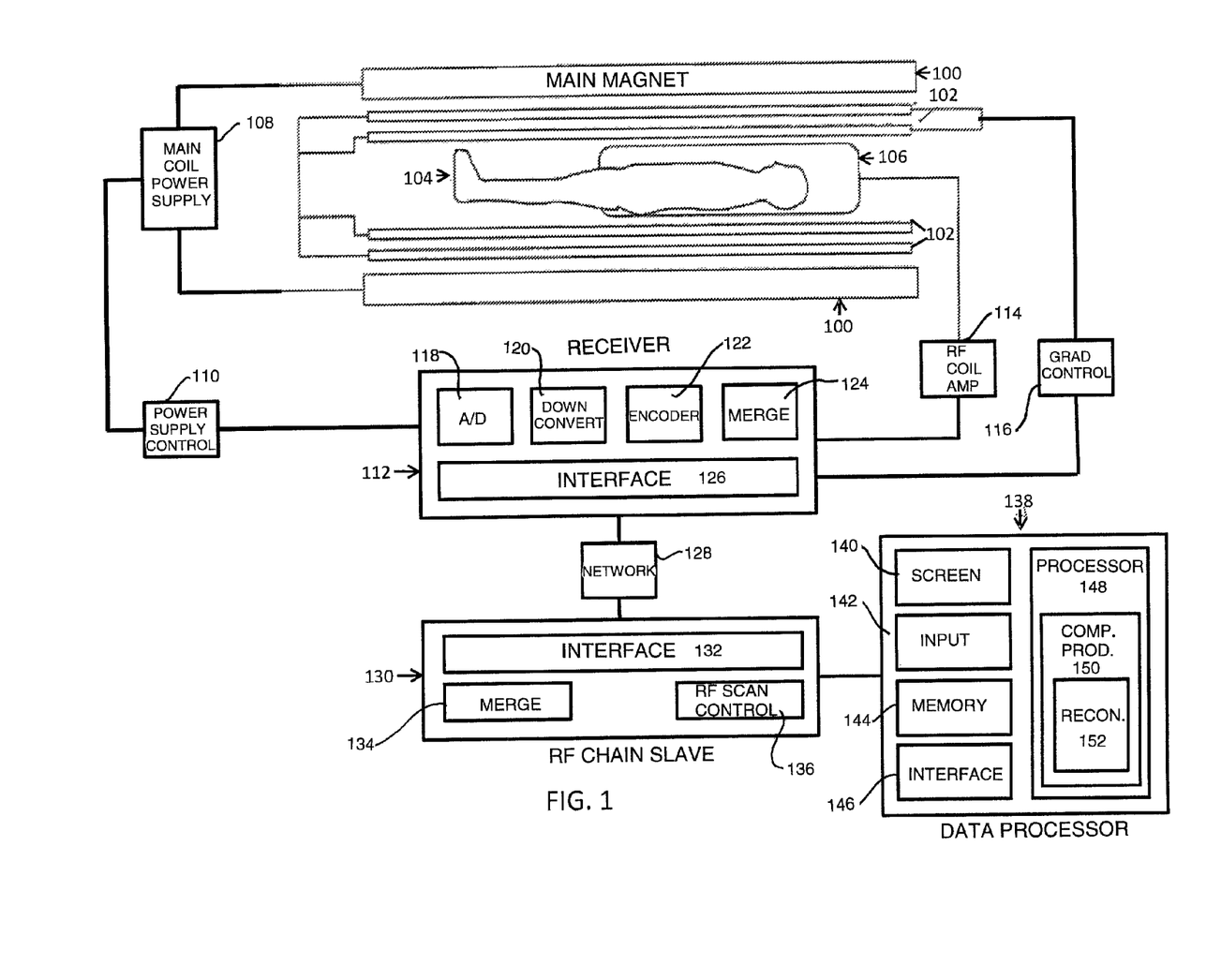
FIG. 1 is a block diagram of a magnetic resonance imaging apparatus.

FIG. 1 is a block diagram of a magnetic resonance imaging apparatus. The magnetic resonance imaging apparatus comprises main magnet coils 100 being appropriate to produce a static magnetic field required for magnetic resonance imaging. The apparatus further comprises gradient coils 102. These gradient coils 102 enable to selectively image different voxels (volume picture elements) of a subject. A patient or more generally a subject 104 is located within a typically cylindrical core of the main magnetic coils 100. Parts of the body of the patient 104 are imaged using a coil 106. Such a coil may comprise a transmit coil and a receiver coil, or alternatively a transmit coil being separated from the receiver coil may be additionally provided.

The main magnet coils 100 are controlled by a main coil power supply 108 and a power supply control 110. The gradient coils 102 are controlled by a gradient coils control unit 116. Also provided is a transmit coil amplifier 114, This transmit coil amplifier 114 is connected to the coil 106. The coil 106 itself can be adapted as a coil comprising many element coils.

The power supply control 110, the transmit control amplifier unit 114 and the gradient coils control unit 116 are connected to a receiver 112. The receiver 112 comprises an Analogue-Digital-Converter 118 being adapted to convert radio frequency (RF) signals received from the coil 106 into digital signals. Using a digital down converter 120, the digitized MR signals can be down converted in order to reduce the data rate from the Analogue-Digital-Converter to a factor 50 or less (from e.g., 50 MHz to 1 MHz). An encoder and/or compressor 122 may even further reduce the bandwidth by making use of the MR signal properties.

The receiver 112 further comprises an element based merge unit 124. The element based merge unit 124 serves the purpose of merging MR data and status data incoming to the receiver with the acquired MR data and the local status and to provide said merged information for further processing to the system. This is especially necessary, when multiple coils are connected to the receiver 112 or when multiple receivers are interlinked.

The receiver 112 further comprises an interface 126. Thereby, the interface 126 is adapted for transmitting for example the down converted digital signal through a communication link over a network 128 to an RF-chain slave subsystem 130. Thereby, the RF-chain slave subsystem 130 also possesses an interface 132. Such kind of interface may be an over the air interface for wireless data transmission or an optical fiber.

The RF-chain slave subsystem 130 comprises an RF scan control unit 136 and a system based merge unit 134. The system based merge unit 134 serves the purpose of merging MR data and status information incoming to the interface 132 from multiple receivers. It also serves the purpose of broadcasting control and status commands to all incoming fibers, said fibers incoming to the interface 132.

The RF-chain slave subsystem 130 is connected to a data processing system 138. The data processing system 138 comprises a screen 140, an input device 142, a memory 144, an interface 146 and a processor 148. The processor 148 comprises a computer program product 150. The computer program product 150 comprises a reconstruction module 152 which reconstructs the magnetic resonance image by using an inverse 2D Fourier Transformation to transform the k-space data into a magnetic resonance image.

Figure 2:
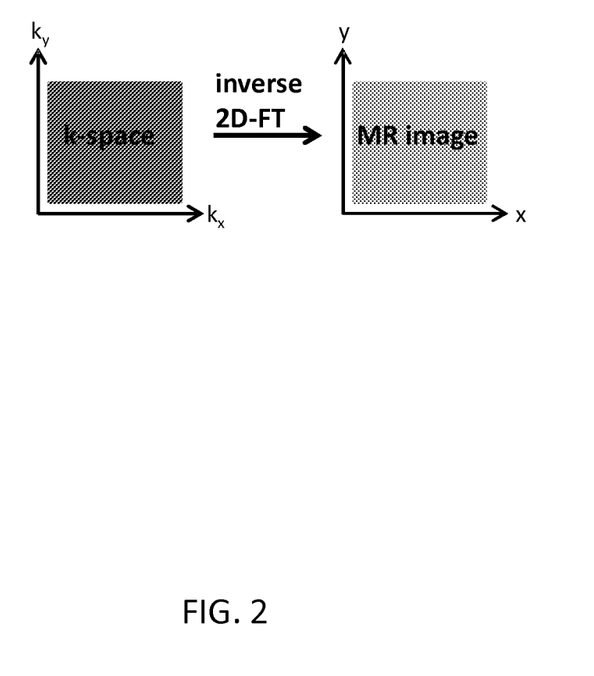
FIG. 2 is a scheme illustrating the creation of k-space data through the sampling of the MR signal.

FIG. 2 is a scheme illustrating the creation of k-space data through the sampling of the MR signal. FIG. 2 shows the principle of reconstruction of a magnetic resonance image. The k-space is the denotation for the raw data matrix in magnetic resonance imaging. These raw data are converted into an MR image using inverse 2D or 3D Fourier transformation. The measured signal includes two informations. Firstly, the frequency encoding gradients include data on the origin of the signal in the x-direction. Secondly, the phase encoding gradients include data on the origin of the signal in the y-direction (and optionally further directions).

All subsampling in the herein disclosed embodiments are performed along the phase encoding direction(s), while the frequency encoding direction is usually fully sampled and processed separately. As a consequence, the described sampling pattern apply primarily to 3D imaging, with frequency encoding direction $k_x$, and phase encoding directions $k_y$ and $k_z$, where the described sampling pattern is applied to points in the $k_y$-$k_z$ plane, where each point actually represents a k-space line along $k_x$ that is fully sampled.

Figure 3:
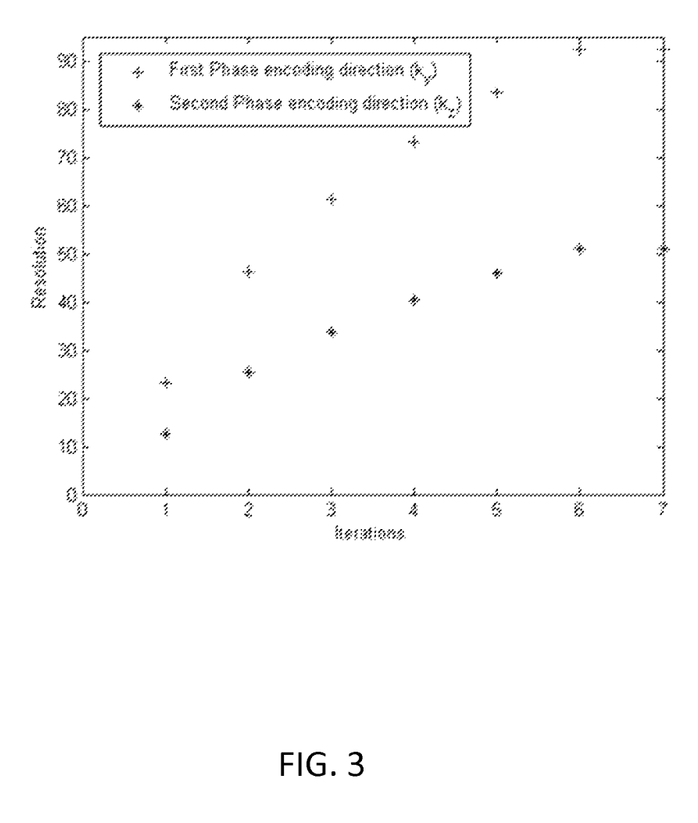
FIG. 3 shows the spatial resolution as function of the iterations.

FIG. 3 shows the spatial resolution as function of the iterations. One sampling procedure with predefined half-axes is called iteration. In detail, this means that the second sampling with the second length of half-axes is the second iteration; the third sampling with the third length of half-axes is the third iteration, and so on. The spatial resolution is restricted by the maximum average reduction factor R and the number of subsets the acquisition is segmented into after sampling the elliptical central area of k-space. Assuming that each subset contains N samples and takes a time T, the spatial resolution increases as $$y_i \propto (iNR+N_0)^{+1/2} \text{ and } z_i = y_i z_0/y_0$$

wherein i is the number of subsets, $N_0$ is the number of samples in the central elliptical area and $y_i$ and $z_i$ are the half-axes after i subsets. The reduction factor is the factor by which the number of k-space samples is reduced. In FIG. 3 the development of the spatial resolution for a maximum reduction factor of 8 and 40 subsets, for an image with $N_y=185$ and $N_z=102$ is plotted. The first phase encoding direction ($k_y$) and the second phase encoding direction ($k_z$) are shown.

Figure 4:
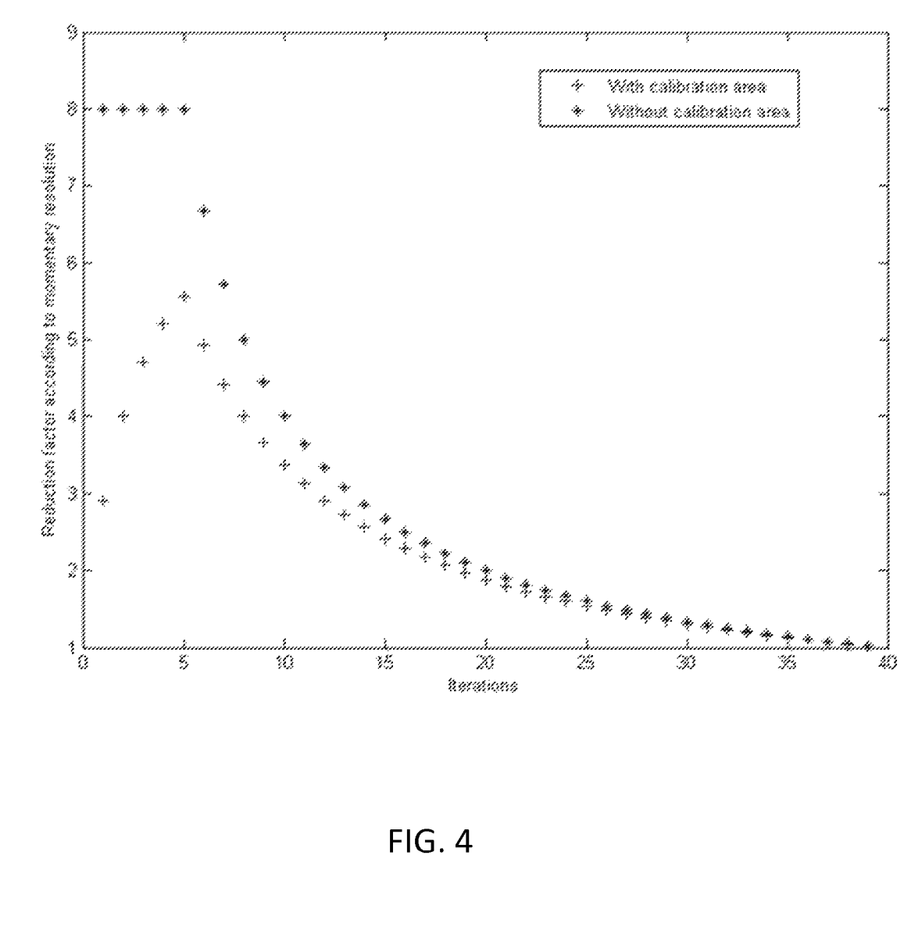
FIG. 4 shows the reduction factor as function of the iterations.

FIG. 4 shows the reduction factor as function of the iterations. As in the description of FIG. 3 mentioned the values are based on a maximum reduction factor of 8 and 40 subsets, for an image with $N_y=185$ and $N_z=102$. Two cases are distinguished in FIG. 4, the reduction factor as a function of the interations with a calibration area and without a calibration area. The underlying nominal number of samples is calculated to the momentary spatial resolution.

Figure 5:
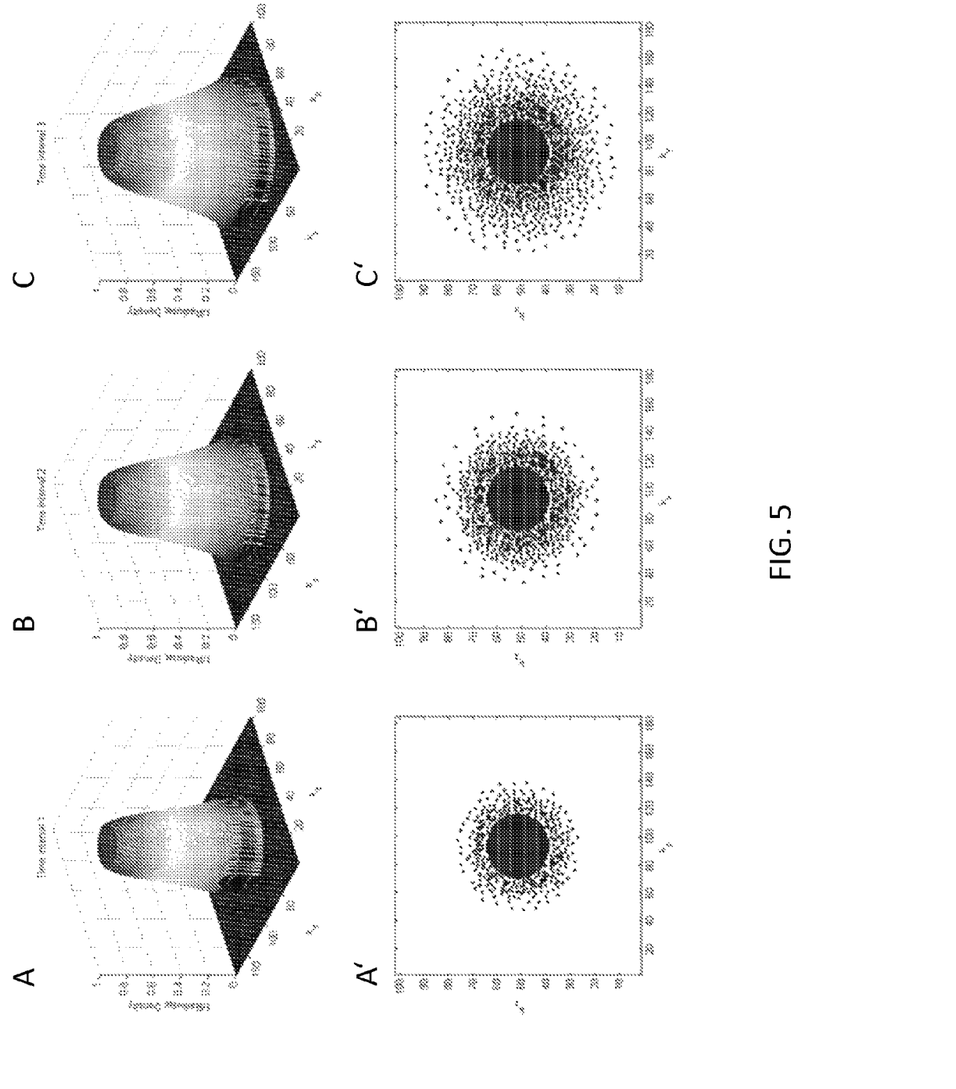
FIG. 5 shows the density of sampling points and the corresponding sampling pattern after 1, 2 and 3 iterations.

FIG. 5 shows the density of sampling points and the corresponding sampling pattern after 1, 2 and 3 iterations. As described also in the description of FIG. 3, the first iteration means the time interval in which the sampling of a peripheral area with predefined half-axes is executed (FIG. 5A). After this sampling the length of the half-axes can be increased and the time interval for the sampling of this peripheral area is the second iteration (FIG. 5B). FIG. 5C shows the third iteration which means that the half-axes are further increased and this defined peripheral area is sampled. The FIGS. 5A, 5B and 5C show the density of the sampling points. The FIGS. 5A', 5B' and 5C' show the sampling pattern in k-space. The distribution of the density of sampled points results from two conditions: the spatial resolution steadily increases over time and the sampling density monotonically decreases toward the periphery of k-space. To generate the sampling pattern a Poisson disk sampling is used herein. Poisson disk sampling is a random distribution of samples with the additional constraint that neigbouring samples must not fall below a defined distance. Due to the above mentioned a central area of k-space is fully sampled. This area may increase over time. The sampling density drops to zero at the edge of the peripheral area respectively at the edge of the half-axes which defines the peripheral area. The random respectively pseudo-random selection of the plurality of points being located in the peripheral area leads to a nearly locally homogeneous subsampling of the peripheral area.

Figure 6:
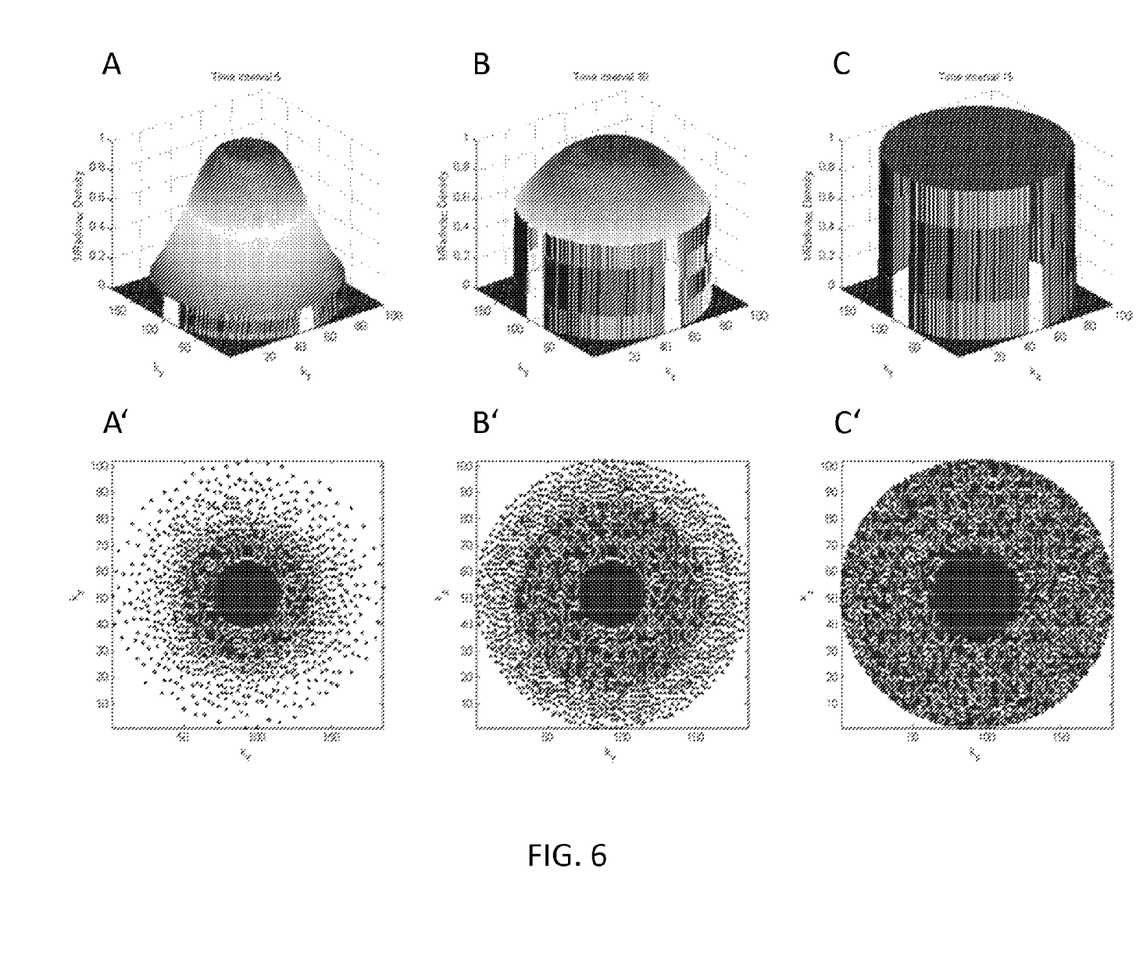
FIG. 6 shows the density of sampling points and the corresponding sampling pattern after 5, 10 and 15 iterations.

FIG. 6 shows the density of sampling points and the corresponding sampling pattern after 5, 10 and 15 iterations. As described before in the description of FIG. 5, iteration means the time interval in which the sampling of a peripheral area with predefined half-axes is executed. The fifth iteration is the sampling of the peripheral area after the length of the half-axes was increased for the fifth time (FIG. 6A). The tenth iteration is the sampling of the peripheral area after the length of the half-axes was increased for the tenth time (FIG. 6B). And finally FIG. 6C shows the density of sampling points and the corresponding sampling pattern after 15 iterations. The FIGS. 6A, 6B and 6C show the density of the sampling points. The FIGS. 6A', 6B' and 6C' show the sampling pattern in k-space. The distribution of the density of sampled points results from two conditions: the spatial resolution steadily increases over time and the sampling density monotonically decreases toward the periphery of k-space. The maximum spatial resolution is defined by the user and the radius of the k-space respectively the length of the half-axes are not increased anymore at a certain point in time when this maximum spatial resolution has been reached. To generate the sampling pattern a Poisson disk sampling is used herein as described above. Both the maximum sampling density near the center of k-space and the decay rate toward the periphery of k-space are adapted in the course of the acquisition, while the averaged reduction factor is successively reduced, as illustrated in FIG. 6. This is continued until the patient starts to breathe again, which can be detected with a respiration sensor, a navigator, or in a series of images produced from successively more data, among others. If the patient is able to hold his/her breath for a really long time then it can be possible that also the peripheral area is fully sampled.

Figure 7:
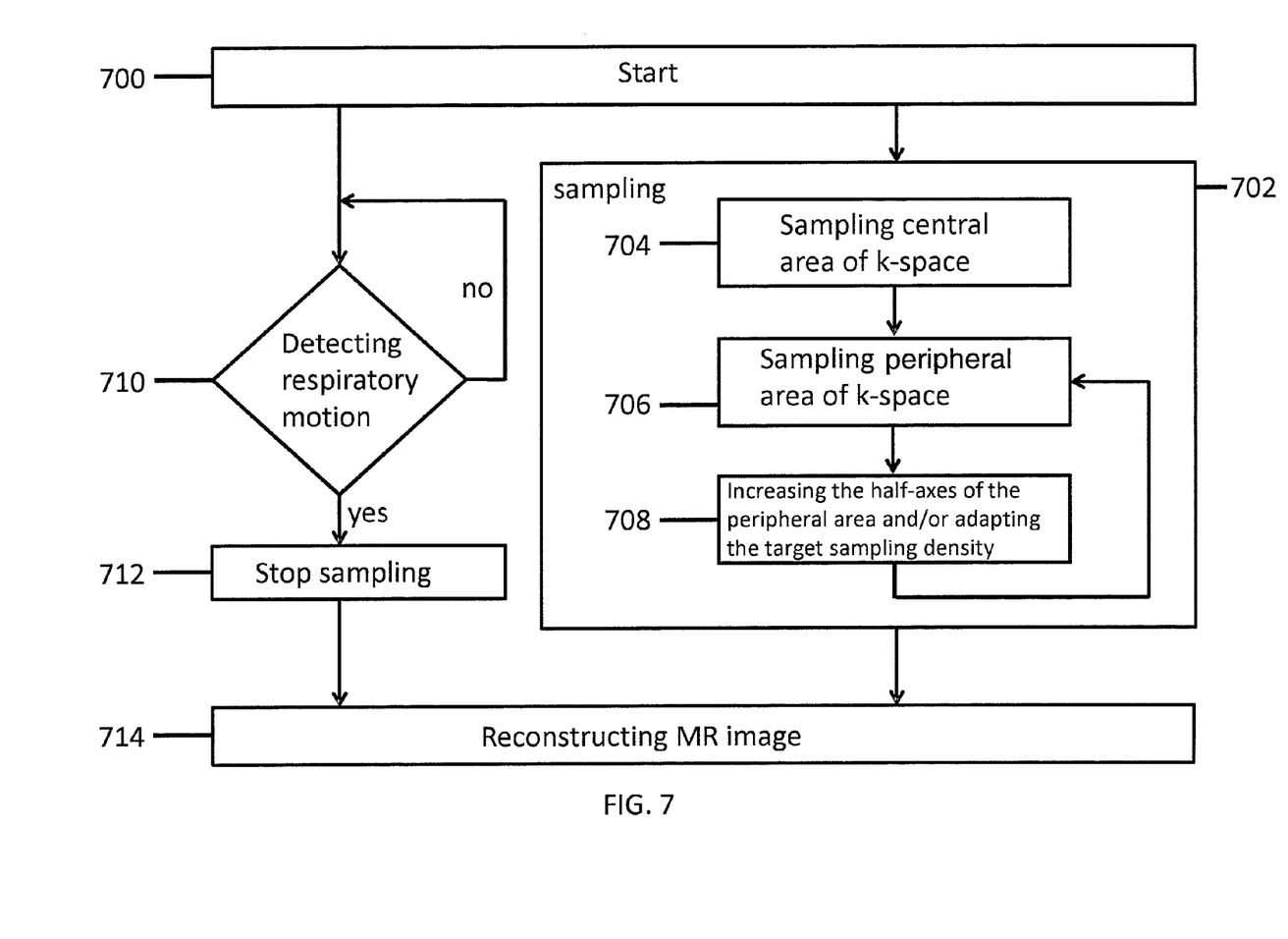
FIG. 7 is a flowchart illustrating the sampling strategy for accelerated magnetic resonance imaging with incomplete breathholds.

FIG. 7 is a flowchart illustrating the sampling strategy for accelerated magnetic resonance imaging with incomplete breathholds. The method starts in step 700 at which the sampling 702 and the detection of respiratory motion 710 start. The sampling 702 comprises the sampling of the central area of k-space 704, followed by the sampling of the peripheral area of k-space 706. After the sampling of the peripheral area of k-space 706, the half-axes of the peripheral area can be increased 708, and the peripheral area of k-space 706 with adapted half-axes is sampled again. This can be repeated until the predefined maximum length of the half-axes is reached and the enclosed k-space area is fully sampled. In addition or alternative to increasing the half-axes of the peripheral area from iteration to iteration, the k-space variant target sampling density can be adapted. During the sampling the respiratory motion is detected in parallel 710. If no respiratory motion is detected the sampling procedure goes on, until respiratory motion is detected. If respiratory motion occurs the sampling will be stopped in step 712. In step 714 the MR image is reconstructed by using the k-space samples acquired before respiratory motion occurred.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of generating a magnetic resonance image of a subject, the method comprising:
during a breathhold, acquiring k-space samples by:
fully sampling an elliptical central area of k-space, wherein the k-space has a plurality of points, each point being representative of a potential sample;
partially sampling an elliptical peripheral area in k-space, wherein the peripheral area surrounds the central area;
said partial sampling of the elliptical peripheral area according to:
random or pseudo-random sampling at a Poisson-disk distribution and a variable density decreasing outward in k-space, at a pre-set sampling reduction factor;
selection of sampling positions outside a pre-selected minimum distance from an already sampled point and minimizing the distance between successively sampled points;
repeating the partial sampling of the elliptical peripheral area, increasing the elliptical peripheral area until:
(a) a pre-set maximum resolution of the acquired k-space samples is reached or
(b) respiratory motion of the subject is detected; and
reconstructing the magnetic resonance image of the subject using the k-space samples acquired before the detection of respiratory motion.

2. The method of claim 1, wherein when the pre-set maximum resolution is reached the partial sampling of the elliptical peripheral area is continued at a decreased reduction factor of the partial sampling density.

3. The method of claim 1, wherein increasing of the elliptical peripheral area includes:
increasing half-axes of the peripheral area during the acquisition over time for increasing spatial resolution over time.

4. The method of claim 1, wherein detecting the respiratory motion includes:
detecting moving of a diaphragm or an abdomen of the subject using a magnetic resonance navigator simultaneously or interleaved with the sampling of the central and peripheral areas of k-space.

5. A non-transitory computer-readable medium carrying software and configured to control a magnetic resonance imaging system to perform the method of claim 1.

6. A medical apparatus for generating a magnetic resonance image of a subject comprising:
a respiratory motion detector configured to detect respiratory motion of the subject;

a controller configured to control an RF scan controller and a gradient controller of a magnetic resonance imaging apparatus to:
    fully sample an elliptical central area of the $(k_y, k_z)$-plane in k-space, wherein the k-space has a plurality of points, each point being representative of a potential sample and where each point of the $(k_y,k_z)$-plane corresponds to a full sampling of a line in k-space along $k_x$;
    partially sample an elliptical peripheral area of the $(k_y,k_z)$-plane in k-space, wherein the peripheral area surrounds the central area, said partial sampling of the elliptical peripheral area according to:
        random or pseudo-random sampling at a Poisson-disk distribution with a variable density decreasing outward in the $(k_y,k_z)$-plane in k-space, at a pre-set sampling reduction factor,
        selection of sampling positions outside a pre-selected minimum distance from an already sampled point and minimizing the distance between successively sampled points,
        repeating the partial sampling of the elliptical peripheral area of the $(k_y,k_z)$-plane, increasing the elliptical peripheral area until a first to occur of:
            (a) a pre-set maximum resolution of the acquired k-space samples is reached or
            (b) respiratory motion of the subject is detected by the respiratory motion detector;
    a processor configured to reconstruct the k-space samples acquired before the detection of respiratory motion into the magnetic resonance image using an acceleration reconstruction technique.

7. An apparatus for generating a magnetic resonance image of a subject, the apparatus comprising:
    a controller configured to, during a breathhold:
        fully sample data in an elliptical central area of k-space,
        partially sample data in an elliptical peripheral area of k-space adjacent the elliptical central area using a Poisson-disk distribution, such that (1) the sampled peripheral area of k-space progressively expands, and (2) the peripheral region of k-space is sampled more densely closer to the elliptical central area and progressively less densely further from the central area;
    wherein the controller is further configured to stop sampling k-space in response to respiratory motion by the subject being detected by a respiratory motion detector; and
    a reconstruction processor configured to reconstruct the data sampled prior to the detection of respiratory motion into the magnetic resonance image.

\* \* \* \* \*